(12) United States Patent
Timm et al.

(10) Patent No.: US 8,062,205 B2
(45) Date of Patent: Nov. 22, 2011

(54) DRUG ELUTION FOR IMPLANTABLE INCONTINENCE DEVICES

(75) Inventors: Gerald W. Timm, Minneapolis, MN (US); David W. Anderson, Brooklyn Park, MN (US); Laura B. Skadsberg, Woodbury, MN (US)

(73) Assignee: GT Urological, LLC, Minneapolis, MN (US)

( * ) Notice: Subject to any disclaimer, the term of this patent is extended or adjusted under 35 U.S.C. 154(b) by 1559 days.

(21) Appl. No.: 11/434,966

(22) Filed: May 16, 2006

(65) Prior Publication Data

US 2006/0264697 A1 Nov. 23, 2006

Related U.S. Application Data

(60) Provisional application No. 60/682,269, filed on May 18, 2005.

(51) Int. Cl.
*A61F 2/02* (2006.01)
(52) U.S. Cl. ............................................. 600/30; 600/37
(58) Field of Classification Search .............. 600/29–32, 600/37; 606/151; 128/897, 898, DIG. 25
See application file for complete search history.

(56) References Cited

U.S. PATENT DOCUMENTS

| | | |
|---|---|---|
| 5,184,629 A | 2/1993 | Erickson et al. |
| 5,509,888 A | 4/1996 | Miller |
| 5,704,893 A | 1/1998 | Timm |
| 5,860,911 A | 1/1999 | Dolade Guardia |
| 6,074,341 A | 6/2000 | Anderson et al. |
| 6,534,693 B2 | 3/2003 | Fischell et al. |
| 2002/0049364 A1 | 4/2002 | Pregenzer et al. |
| 2003/0108588 A1 | 6/2003 | Chen et al. |
| 2004/0173219 A1 | 9/2004 | Bakane |
| 2005/0038452 A1* | 2/2005 | Chu .............................. 606/151 |

FOREIGN PATENT DOCUMENTS

WO WO 02/02031 A1 1/2002

OTHER PUBLICATIONS

Supplementary European Search Report issued by the European Patent Office Apr. 22, 2009 in co-pending European Patent Application No. 06759891.

* cited by examiner

*Primary Examiner* — Charles A Marmor, II
*Assistant Examiner* — Carrie R Dorna
(74) *Attorney, Agent, or Firm* — Hamre, Schumann, Mueller & Larson, P.C.

(57) ABSTRACT

An implantable incontinence device and method provides for occluding the urethra in preventing urine leakage. The device includes an occluding member connected to a control mechanism. The occluding member is movable from a contracted (occlusive) condition to an expansive (non-occlusive) condition by activating and deactivating the control mechanism. A drug coating is disposed on a portion of the implantable incontinence device. The drug coating elutes a bioaffecting or pharmaceutical composition to minimize capsular tissue formation, so that prevention of urine leakage can be facilitated.

13 Claims, 10 Drawing Sheets

Detail A

DRUG ELUTION FOR IMPLANTABLE INCONTINENCE DEVICES

CROSS REFERENCE TO RELATED APPLICATIONS

The present application draws priority from U.S. Provisional Patent Application Ser. No. 60/682,269, filed May 18, 2005, and entitled "Drug Eluting Incontinence Device", which is herewith incorporated by reference in its entirety.

This invention was made with government support under SBIR Grant Number 1R43DK067699-01A1 awarded by the National Institutes of Health. The government has certain rights in the invention.

FIELD

The technical disclosure relates to drug elution for implantable incontinence devices. More particularly, the disclosure relates to drug elution for minimizing capsular formation on an incontinence device in the prevention of urine leakage.

BACKGROUND

Incontinence devices are known and have included such implanted devices that contract the urethra to prevent urinary leakage or that contract the bowel to prevent fecal leakage. Similarly, the esophagus may be contracted to prevent gastroesophageal reflux (GER). These devices are commonly referred to as "artificial sphincters" and are installed within the body to aid or replace the body's natural sphincter.

One such type of artificial urinary sphincter is described in U.S. Pat. Nos. 5,704,893 & 6,074,341 both entitled "Vessel Occlusive Apparatus and Method." A device of this type was entered into human clinical trials by Timm Medical Technologies, Inc. However, its proper function was impeded by growth of a constricting tissue capsule around its mechanisms, due to the natural defenses of the human body. The human body ordinarily exhibits a defense mechanism by causing a tissue capsule to form around the synthetic structures of man-made implantable devices in an attempt to wall it off from the rest of the body.

Attempts have been made to minimize tissue capsule growth around medical devices by impregnating them with various drugs intended to interrupt cellular processes causing capsular formation. Several examples have included using the drug Sirolimus (Rapamycin) are described in U.S. Pat. No. 6,534,693 "Surgically Implanted Devices Having Reduced Scar Tissue Formation." Sirolimus is also currently being used in intravascular coronary stents to prevent restenosis of coronary arteries, which typically accompanies coronary angioplasty and coronary artery stenting.

Further, the anti-inflammatory drug dexamethasone has a long history in the reduction of inflammatory response and subsequent capsular formation around implanted devices. For example, it is used in Medtronic, Inc. (Minneapolis, Minn.) Intra Coronary Defibrillation (ICD) leads and Endotak Reliance® Tined Endocardial Defibrillation ICD leads produced by Guidant Corporation (St. Paul, Minn.). The drug is intended to prevent formation of tissue capsules with high electrical impedance around the electrode. Abbott Laboratories, Inc. (Redwood City, Calif.) has entered its BiodivYsio dexamethasone-eluting intracoronary stent into clinical trials and demonstrated its ability to minimize coronary restenosis.

While it appears that such drugs have largely been employed in stenting and coronary implant procedures, advancements may yet be made to employing these principles in other applications, such as in implantable incontinence devices.

SUMMARY

It is the purpose of the present technical disclosure to provide an improved incontinence device that includes drug elution capability for minimizing capsular formation around the structures of the device, so that the function of the device is not impeded, and so that prevention of urine, bowel or esophageal leakage can be facilitated.

Generally, a drug eluting implantable incontinence device is inserted or surgically implanted within the body for controlling the lack of urinary, bowel or esophageal restraint. The device includes an occluding member that acts as the "artificial sphincter" and a control mechanism for controlling the occluding member to open or close an annular opening, such as a urethra. Additionally, the drug eluting implantable incontinence device incorporates a pharmaceutical or bioaffecting composition thereon.

The bioaffecting composition is capable of reducing or preventing abnormal pathologic conditions of the living body, including for example inflammatory response and subsequent capsular formation when foreign structures are introduced into the body. The effect of the abnormality may be limited by chemically altering the physiology of the host, such as by differential release of the active pharmaceuticals through a membrane or diffusion barrier.

In one embodiment, an incontinence device for preventing urinary, bowel or esophageal leakage includes an occluding member, a control mechanism, and a drug coating. The occluding member is implanted in a host and disposed around a bodily duct for exiting waste. The control mechanism is operatively connected with the occluding member, and is implanted in the host. The control mechanism controls the occluding member to close the bodily duct in an occluded state or to open the bodily duct in a non-occluded state. The drug coating includes a bioaffecting composition thereon. The drug coating may be disposed as a layer on an outer surface of at least one of the occluding member and control mechanism. The drug coating elutes the bioaffecting composition into surrounding tissue of the host.

In one embodiment, the host is a human male or female and the bodily duct is the urethra or bladder neck, in which the device prevents urinary leakage.

In one embodiment, the occluding member may be a tape member or sheath that encircles the bodily duct after being implanted. The tape member or sheath includes a preset radial occlusive force imparted thereon to suitably contract and close the bodily duct. In yet another embodiment, the tape member has a width dimension that is greater than a thickness direction.

In one embodiment, the control mechanism comprises an activator, a deactivator, and a tensioning member controlled by the activator and deactivator and connected to the occluding member. The deactivator may move the occluding member to the non-occluded state by releasing a tension from the tensioning member, thereby releasing the preset radial occlusive force from the occluding member. The activator may move the occluding member to the occluded state by returning tension to the tensioning member, thereby returning the preset radial occlusive force to the occluding member.

In one embodiment, the drug coating is disposed on both the occluding member and control mechanism.

In yet another embodiment, the drug coating includes a porous polymeric membrane disposed over the drug coating.

The porous membrane includes a pore size that controls an elution rate of the bioaffecting composition.

A method of controlling a bodily duct to enable or disable urinary, bowel or esophageal movement includes implanting an incontinence device into a bodily host. The incontinence device includes an occluding member operatively connected to a control mechanism and a drug coating disposed on at least one of the occluding member and control mechanism. The drug coating includes a bioaffecting composition thereon. The method includes activating the incontinence device, using the control mechanism, to move the occluding member to an occluded state, thereby disabling urinary, bowel or esophageal leakage; and deactivating the incontinence device, using the control mechanism, to move the occluding member to a non-occluded state, thereby enabling urinary, bowel or esophageal leakage. The method further includes eluting the bioaffecting composition into surrounding tissue of the bodily host.

The inventive principles of the present disclosure provide an incontinence device wherein the drug coating can minimize capsular formation resulting from a bodily response of the host. In turn, the drug coating can facilitate function of the incontinence device in preventing urinary, bowel or esophageal leakage by preventing the structures of the device from being impeded by any capsular formation.

These and other various advantages and features of novelty, which characterize the incontinence device, are pointed out in the following detailed description. For better understanding of the device, its advantages, and the objects obtained by its use, reference should also be made to the drawings which form a further part hereof, and to accompanying descriptive matter, in which there are illustrated and described specific examples of the device in accordance with the inventive principles.

BRIEF DESCRIPTION OF THE DRAWINGS

Like reference numbers generally indicate corresponding elements in the Figures. The embodiments illustrated are exemplary only and are in accordance with the principles of the present invention.

DETAILED DESCRIPTION

Figure 1:
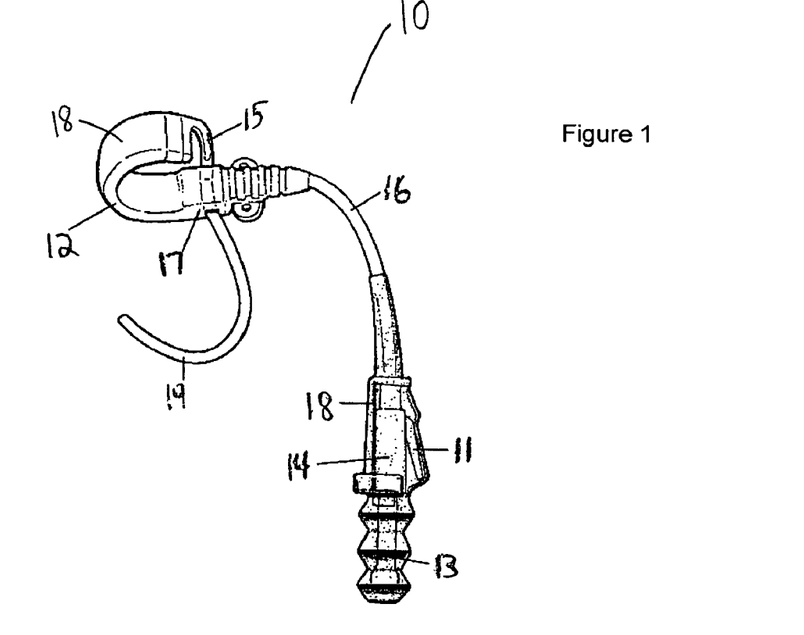
FIG. 1 represents an elevational view of one embodiment of a drug eluting implantable incontinence device.
Figure 2:
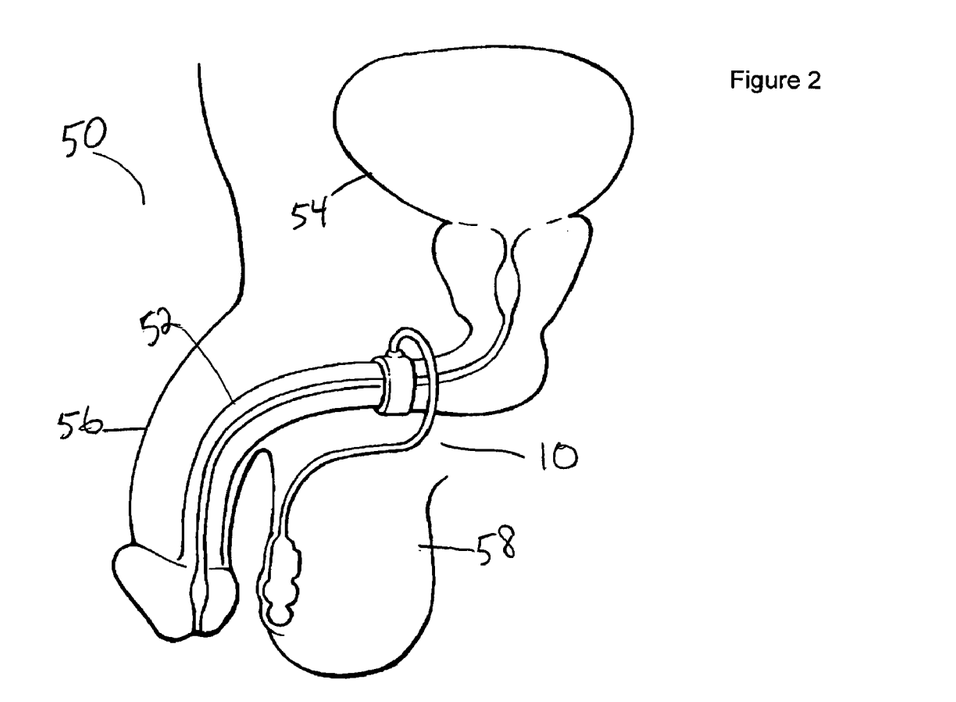
FIG. 2 represents the device of FIG. 1 implanted in a male and showing one embodiment of an occluding member of the device disposed around the male urethra.

One exemplary embodiment of an incontinence device 10 is provided in FIGS. 1-4B and 6A-6B. FIGS. 1 and 2 respectively illustrate an elevational view of the incontinence device 10 and show the device 10 implanted in a male human 50. The device 10 is implanted on the urethra 52 and downstream from the bladder 54. It will be appreciated that the host may be a female host in which the device may be suitably implanted on the female urethra and in the labia area.

The incontinence device 10 includes an occluding member 12 and a control mechanism 14 connected to the occluding member 12 by a conduit tube 16. A drug coating 18 may be disposed on the outer surface of at least one of the occluding member 12 and control mechanism 14. As shown, the drug coating 18 is disposed on both the occluding member 12 and control mechanism 14. However, it will be appreciated that the drug coating 18 may be limited to being disposed on the outer surfaces of any number of structures of the device 10, and it will be further appreciated that the drug coating may be disposed on an outer surface of the entire device. Further details of the drug coating 18 are discussed below.

The occluding member 12 may be an implanted sheath that encircles the urethra or bladder neck. The sheath includes a locking clip 15 and guide tab 19 that may be used to hold the sheath in an encircling position and onto a shroud portion 17. In one example shown in FIG. 2, the locking clip 15 and guide tab 19 are disposed at a free end of the sheath, and hold the free end onto the shroud portion 17 disposed at another end of the sheath. It will be appreciated that the mechanical structures of the locking clip 15, guide tab 19, and shroud portion 17 are exemplary only, as other mechanical structures may be equally or more suitable for maintaining the encircling position of the sheath.

The occluding member 12 may move between an expanded (urethra open and not occluded) and contracted (urethra closed and occluded) position. As one example only, the occluding member 12 is designed to provide a biasing or spring-like force, that in the activated position, exerts a preset radial occlusive force sufficient to prevent urinary leakage out of the penis 56 (or vagina for female). A sufficient amount of force may be dependent upon the cuff width of the urethra, which can help determine the surface area contact the occluding member will have with the urethra. In an exemplary embodiment, a contact pressure in the range of 50-70 cm $H_2O$ has been successful in contracting the urethra while minimizing atrophy and erosion. In some examples, a force in the range of 0.3 lbs to 1.0 lbs has been able to achieve such pressures. In one embodiment, the occluding member 12 may be manufactured from, but is not limited to, an expanded polytetrafluoroethylene (PTFE) covered with a thin layer of silicone rubber. This material can help provide the preset radial occlusive force. It will be appreciated that the mentioned materials for manufacture are exemplary only. Other materials may be employed that are equally or more suitable in providing the desired preset radial occlusive force.

The occluding member 12 may include a drug coating 18 disposed thereon. In one example shown in FIGS. 3A-3D, the drug coating 18 may be a thin layer which is disposed directly on an outer surface of the occluding member 12 and covering the same. The drug coating 18 includes a bioaffecting composition or pharmaceutical agent incorporated in its matrix or polymeric interstices. Preferably, the drug coating 18 holds the composition within the thin layer. The drug coating 18 slowly elutes the bioaffecting composition or pharmaceutical agent through the matrix or polymeric interstices of the thin layer and into the surrounding tissue under the influence of an osmotic gradient. Elution of the bioaffecting composition into the surrounding tissue of the host can interrupt the defense mechanism response so as to minimize capsular tissue growth on the incontinence device 10.

Figure 3A:
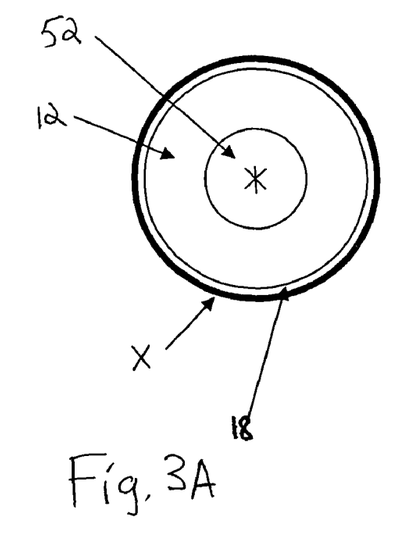
FIG. 3A represents a sectional view of the occluding member shown in a contracted or occluded configuration, and including one embodiment of a drug coating disposed thereon.
Figure 3B:
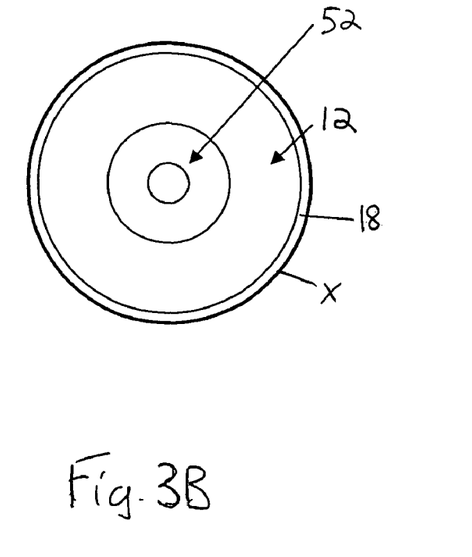
FIG. 3B represents a sectional view of the occluding member of FIG. 3A shown in an expanded or non-occluded configuration.

Preferably, the drug coating 18 is disposed on the occluding member 12, in a manner so as to allow the bioaffecting composition to elute into the surrounding tissue over a prescribed period of time (described below). As shown in FIGS. 3A-B for example, a capsular tissue "X" may be minimized so as to allow the occluding member 12 to move unimpeded in the occluded and non-occluded states. FIG. 3A shows the urethra 52 in the occluded state, while FIG. 3B shows the urethra in the non-occluded state.

Figure 3C:
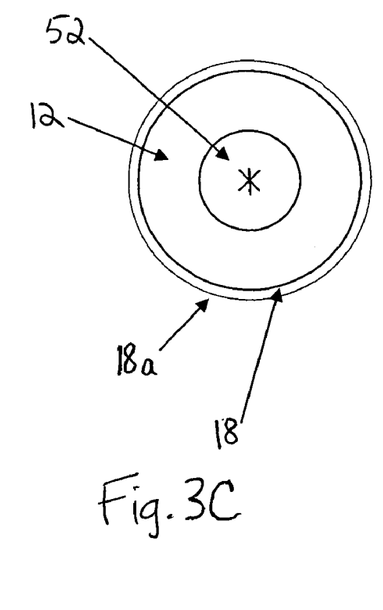
FIG. 3C represents a sectional view of the occluding member of FIG. 3A and including one embodiment of a porous membrane disposed over the drug coating as an outer layer. The device is illustrated in the occluded configuration.
Figure 3D:
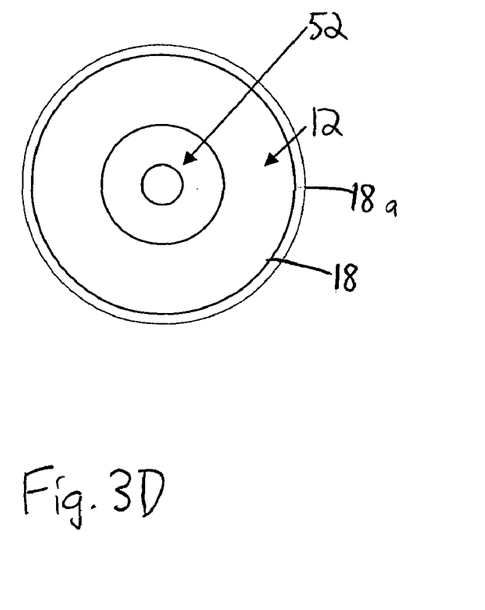
FIG. 3D represents a sectional view of the occluding member of FIG. 3A and including the porous membrane of FIG. 3C disposed over the drug coating as an outer layer. The device is illustrated in the non-occluded configuration.

In another embodiment, FIGS. 3C-D illustrate the occluding member 12 having an additional porous membrane 18a deposited over the drug coating 18. The porous membrane 18a can further control elution of the bioaffecting composition from the drug coating 18. The elution rate may be controlled by varying the membrane pore size. In an exemplary configuration, the membrane pore size may be 1 to 100 μm.

As one example, the porous membrane is a polymeric material. It will be appreciated that a number of materials may be suitably employed for obtaining the desired pore size to control the elution rate. FIG. 3C shows the urethra 52 in the occluded state, while FIG. 3D shows the urethra in the non-occluded state.

In some exemplary configurations, the drug coating 18 may be a polymer that is painted, sprayed or dipped onto the outer surface of the occluding member 12. In another example, the drug coating may be composed of a thin silicone layer having the bioaffecting composition therein. It will be appreciated that the drug coating 18 may remain adherent to the outer surface of the occluding member 12, despite circumferential expansions and contractions including expansions/contractions of up to 30%. Such drug eluting coatings are available by such companies as Surmodics, Inc. (Eden Prairie, Minn.), ISURTEC (St. Paul, Minn.) and AST Products, Inc. (Billerica, Mass.). A variety of drugs including, but not limited to, rapamycin and dexamethasone may be incorporated into the silicone layer or polymeric layer for elution into the surrounding tissues in a controlled fashion.

Figure 5:
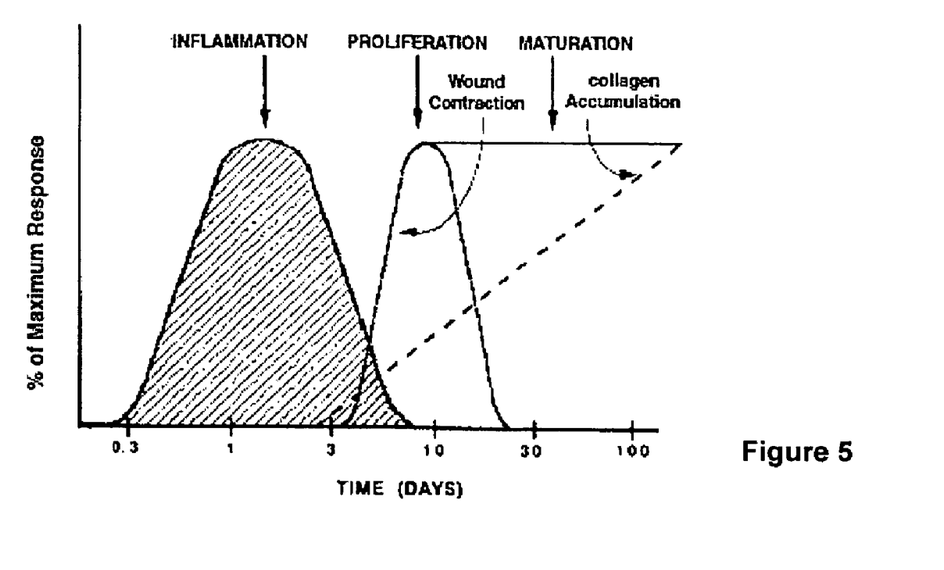
FIG. 5 represents a graph of phases in tissue healing and tissue encapsulation processes.
Figures 6A, 6B:
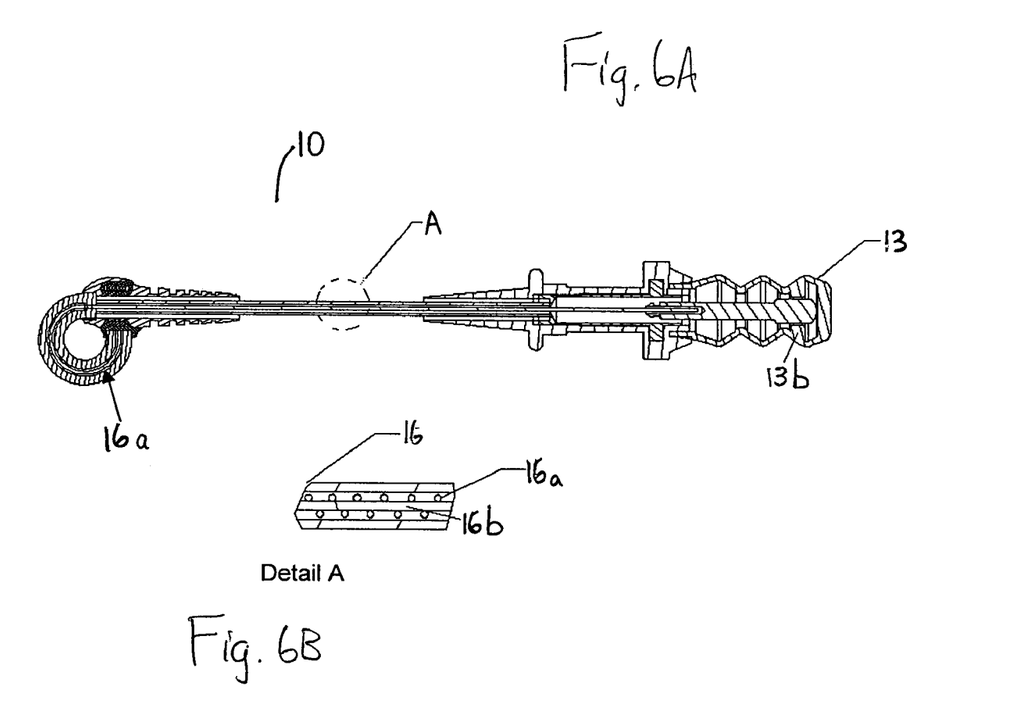
FIG. 6A represents a side sectional view of the device of FIG. 1 and showing one embodiment of a control mechanism and showing one embodiment of a tensioning member operatively connecting the deactivation element with the occluding member.
FIG. 6B represents a sectional view of the control mechanism of FIG. 6A.

The tissue healing process/tissue encapsulation process has been widely investigated and is known to include several different phases as shown in FIG. 5. The tissue encapsulation process may be impeded by disrupting the inflammatory and proliferation phase or both.

Dexamethasone, as one of the above examples, may be incorporated into the drug coating 18 to inhibit the inflammatory phase. As one example, it is preferable that dexamethasone is capable of eluting for approximately 1 week, and including an initial concentration of approximately 0.5 $\mu g/mm^2$. In yet another example, rapamycin may be incorporated into the matrix to elute over a period of approximately 10 to 20 days at an initial concentration of approximately 2.5 $\mu g/mm^2$.

It will be appreciated that a combination of both of these drugs may be incorporated into the matrix to impede both inflammatory and proliferative phases, and each may elute with the same initial concentrations as stated above for each drug alone. It will further be appreciated that employing dexamethasone and rapamycin are examples only, as other drugs or pharmaceuticals may be equally or more suitable in obtaining the similar effects. In any of these examples, once a drug composition has eluted, the biological capsule forming mechanism has effectively been interrupted so that no capsule is formed or at least formation is minimized. Thus, in one embodiment, it may not be necessary to replenish the bioaffecting composition or pharmaceutical agent. However, it will be appreciated that in some applications further drug administration may be required, for instance to continue preventing capsulation locally.

Turning to the control mechanism 14, FIG. 1 shows that an activator 11 and deactivator 13 may be implanted in the scrotum 58 (or labia for a female). The conduit tube 16 mechanically connects the occluding member 12 to the activator 11 and deactivator 13 through a tensioning member in the conduit 16.

The activator 111 and deactivator 13 may be encased within a boot-like structure. Preferably, the control mechanism 14 is primarily composed of a flexible silicone material which acts to prevent tissue in-growth into the mechanism. To urinate, a patient may grasp the general structure of the control mechanism 14 with one hand and, with the other hand, press the deactivator 13 to release the occlusive force of the occluding member 12. Operation of the control mechanism 14 is further described below.

As shown in FIGS. 6A-7B, by pressing the deactivator 13 a tensioning member, including coil 16a and support 16b, can advance through the conduit tube 16 toward the occluding member 12. As the tensioning member advances, it expands the occluding member 12 away from the urethra or the bladder neck, thus releasing the preset occlusive force. After urinating, the patient may press the activator 11 (shown in FIGS. 1 and 2). By pressing the activator 11, the coil 16a and support 16b can retract back to their original positions, so as to reestablish the preset occlusive force on the urethra and close the opening of the same.

Figure 7A:
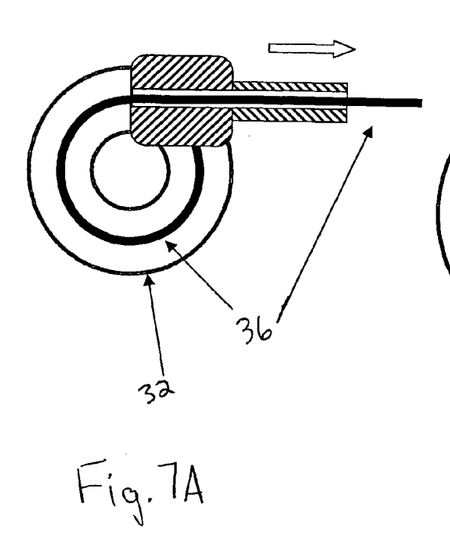
FIG. 7A represents a sectional schematic view of a tensioning member and schematically showing the operation of the tensioning member on the occluding member, where the occluding member is in the contracted state.
Figure 7B:
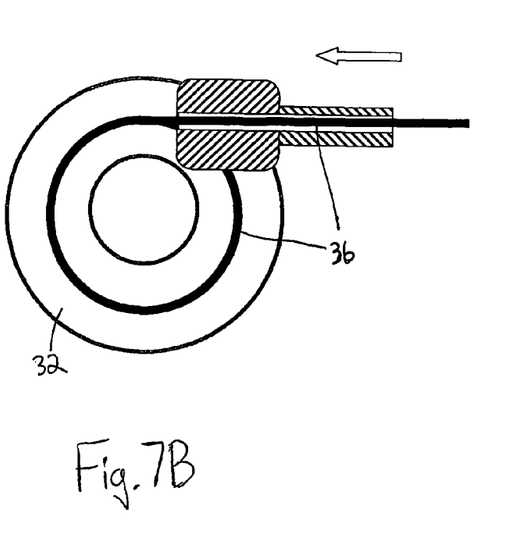
FIG. 7B represents a sectional view of the tensioning member and schematically showing the operation of the tensioning member, where the occluding member is in the expanded state.

FIGS. 7A-B schematically illustrate this movement concept by showing an occluding member 32 contracted and expanded. A tensioning member 36 can advance toward or retract away from the encircled occluding member 32. The arrows indicate the direction of the tensioning member 36 during activation and deactivation. FIG. 7A shows the occluding member in the contracted state, while FIG. 7B shows the urethra in the expanded state.

Preferably, the deactivator 13 is a plunger mechanism encased within pleated bellows 13a. The pleated bellows 13a may also be manufactured of a silicone material to prevent tissue in-growth. It will be appreciated that other materials may be employed that are equally or more suitable to obtain the desired effect. Depression of the plunger by pressing through the scrotal skin imparts movement on the tensioning member, thereby causing the occluding member to expand and release occlusive pressure from the urethra and allow normal urination. Preferably, the activator 11 is a button that, upon depression, imparts movement on the tensioning member to allow the occluding member to contract and reapply urethral pressure in preventing urine leakage.

As with the occluding member 12, a tissue capsule may form around pleated bellows of the deactivator plunger. Such a condition would impede the pleated bellows from fully seating against one another, and would thus prevent the deactivation plunger from being fully depressed and functioning properly. In this instance, a similar drug coating may be applied to the deactivator plunger to prevent tissue capsule bulk formation from impeding plunger function.

Figure 4A:
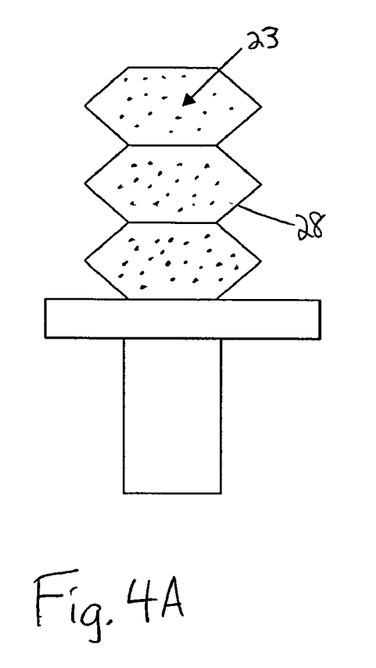
FIG. 4A represents a schematic view of one embodiment of a deactivation element for the device of FIG. 1 and shown at a resting state, such that the occluding member may be in the occluded state.
Figure 4B:
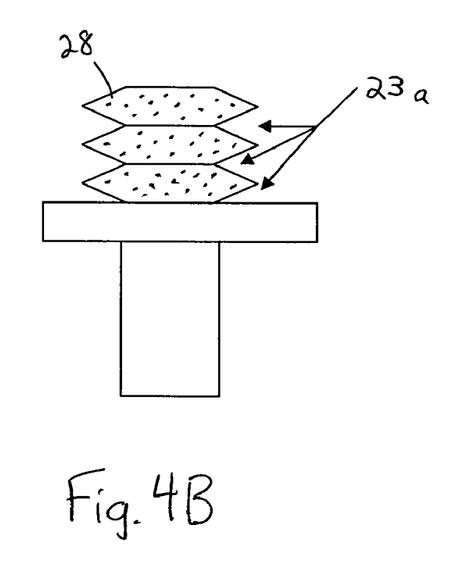
FIG. 4B represents a schematic view of the deactivation element of FIG. 4A and shown in a depressed state such that the occluding member may be expanded.

For example, FIG. 4 illustrates a plunger deactivator 23 having the pleated bellows 23a. A drug coating 28 can be disposed about an outer surface of the plunger. In this configuration, capsular tissue may be prevented from formation on the pleated bellows. It will be appreciated that the drug coating 28 may be similar to that described above for the occluding member and other structures. The drug coating 28 may be applied to the tissue contacting surfaces of the pleated bellows, thereby minimizing the amount of capsular tissue formation around the bellows.

FIGS. 8A-10B represent another embodiment of a urinary incontinence device 100. The urinary incontinence device 100 is illustrated as an implantable device adapted for controlling urine exit through the urethra 152.

Figure 8A:
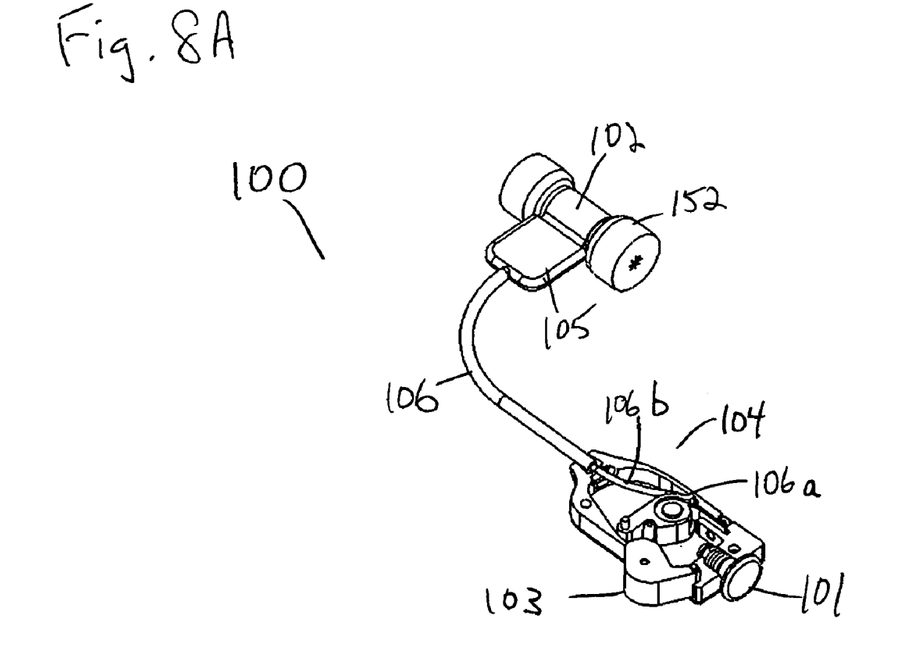
FIG. 8A represents an elevational view of another embodiment of a drug eluting implantable incontinence device, where one embodiment of an occluding member surrounds a urethra in an occluded state.
Figure 8B:
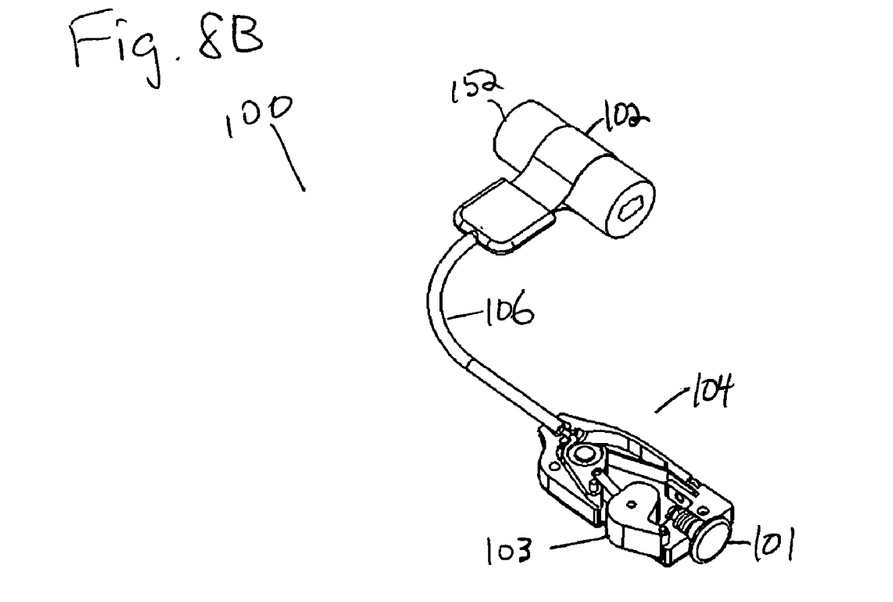
FIG. 8B represents an elevational view of the device of FIG. 8A, where the occluding member is in a non-occluded state.

As with the incontinence device 10, the urinary incontinence device 100 may be implanted in males or females suffering from stress urinary incontinence. The device 100 includes an occluding tape member 102 operatively connected to a control mechanism 104. The occluding tape member 102 encircles the urethra or bladder neck after being implanted. The control mechanism 104 may be implanted in the scrotum, labia or other subcutaneous space overlying the abdomen. A conduit tube 106 joins the occluding tape member 102 and control mechanism 104. It will be appreciated that the incontinence device 100 may also employ a drug coating on any of the device structures in the same manner as with incontinence device 10.

The occluding tape member 102 can be designed to provide a preset radial occlusive force sufficient to prevent urinary leakage through the urethra 152. A sufficient amount of force may be dependent upon the cuff width of the urethra, which can help determine the surface area contact the occluding member will have with the urethra. As one example, a contact pressure in the range of 50-70 cm $H_2O$ has been successful in contracting the urethra while minimizing atrophy and erosion. In some examples, a force in the range of 0.3 lbs to 1.0 lbs has been able to achieve such pressures. The tape member 102 may move between a non-occluded (deactivated) and occluded (activated) position. FIG. 8A shows the urethra 152 in the occluded state, while FIG. 8B shows the urethra 152 in the non-occluded state.

In one embodiment, the tape member 102 is connected to a housing 105. The housing 105 includes an inner space for receiving the tape member 102 when the tape member 102 exerts its preset radial occlusive force to close the urethra 152 in the occluded state, and for releasing the tape member 102 from its preset radial occlusive force to open the urethra in the non-occluded state.

In one example, the control mechanism 104 includes an activator button 101, a deactivator button 103, and a tensioning member 106b controlled by the activator 101 and deactivator 103 buttons. Preferably, the activator 101 and deactivator 103 buttons are mechanically connected to the tensioning member 106b for moving the tensioning member 106b and the occluding tape member 102. The deactivator button 103 can release the tape member 102 from the occluded state by releasing tension from the tensioning member 106b, thereby releasing the preset radial occlusive force of the tape member 102 on the urethra 152. The activator button 101 can return the tape member 102 to the occluded state by returning tension to the tensioning member 106b, thereby returning the preset radial occlusive force of the tape member 102 on the urethra 152.

Figure 10A:
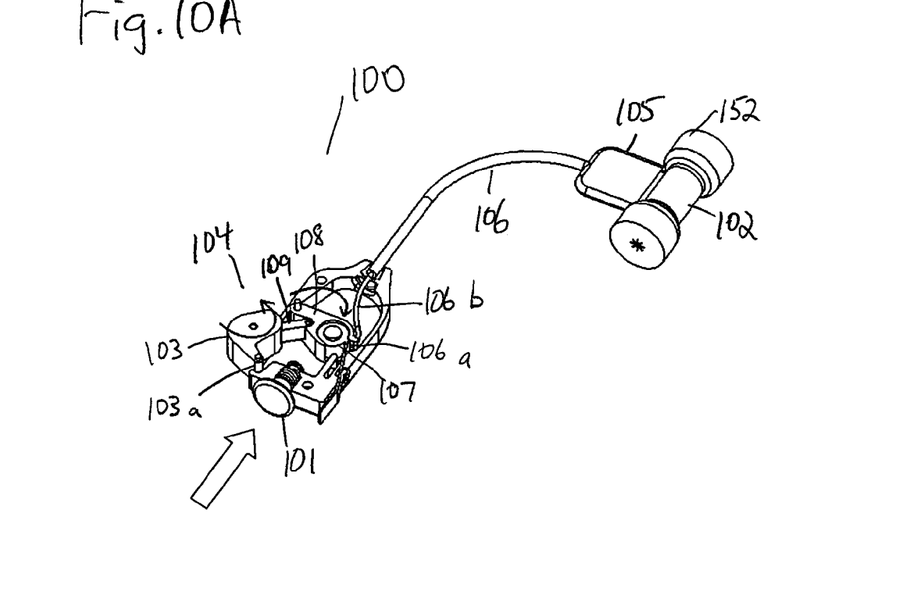
FIG. 10A represents another elevational view of the device of FIG. 8A, and showing one embodiment of a control mechanism in operation, where the occluding member is in the contracted state.
Figure 10B:
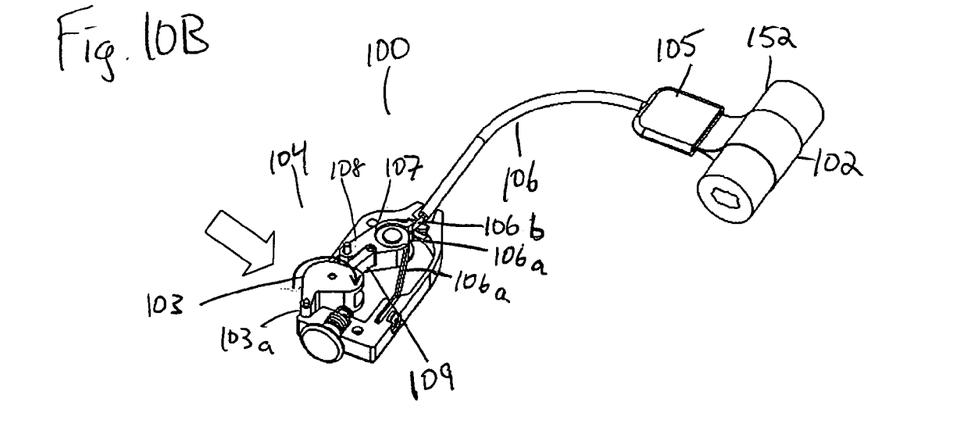
FIG. 10B represents another elevational view of the device of FIG. 8A, and showing the control mechanism in operation, where the occluding member is in the expanded state.

In one embodiment, operation of the control mechanism 104 is as follows. To urinate, the patient can grasp the general structure of the control mechanism 104 and, with the other hand, press the deactivator button 103. This action advances a constant force biasing member 106a to remove tension from the tensioning member 106b. Advancement of the constant force biasing member, via a mechanical linkage connected to the deactivator button 103 (described below), removes tension from the tensioning member 106b through the conduit tube 106. In one embodiment, the constant force biasing member 106a is a nickel-titanium alloy or stainless steel constant force spring, and the tensioning member is a tension cord passing through the conduit tube 106.

The movement described allows the occluding tape member 102 to unfurl from the housing 105. As a result, the urethra 152 may expand and open to enable urine to be expelled from the bladder. Following urination, the patient can press the activator button 101 to reapply a load from the constant force biasing member 106a to the tensioning member 106b. The tensioning member can then pull the occluding tape member 102 within the housing 105.

Figure 9A:
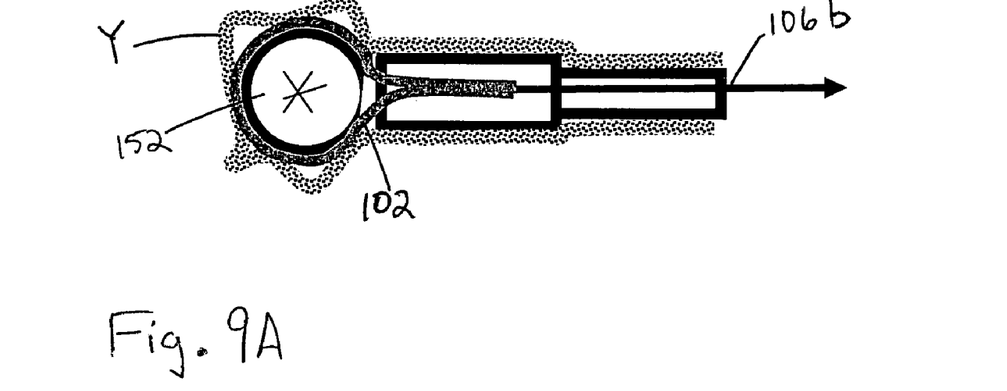
FIG. 9A represents a schematic sectional view of the occluding member shown in a contracted configuration.
Figure 9B:
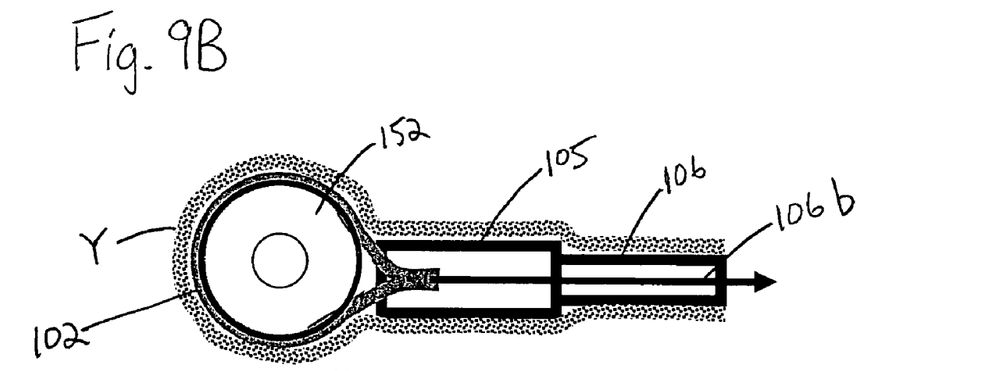
FIG. 9B represents a schematic sectional view of the occluding member shown in an expanded configuration.

As shown in FIGS. 9A-B, by moving the tape member 102 back into the housing 105, the tape member may also move away from any capsular formation "Y" around the device 100. This movement effectively reduces the tape member 102 circumference and re-occludes the urethra 152. Reducing the tape member 102 circumference by having it pull into or out of the housing 105 can also obviate difficulties in device function that may be encountered with capsular formation.

The mechanical linkage structure for the control mechanism is described as follows. It will be appreciated that the mechanical linkage may be any number of mechanical configurations for obtaining the desired effect of imparting and releasing tension on the tensioning member 106 to move the occluding tape member 102 into a smaller and larger circumference.

As one example shown in FIG. 10B, pressing the deactivator button 103 can cause the button 103 to rotate about its pivot 103a, thereby pushing a center linkage 109 forward. The center linkage 109 pushes a spring linkage 107 in a generally arcuate direction about a spring linkage pivot 108. The constant force biasing member 106a may be coiled spring mounted on the spring linkage 107. The constant force biasing member may further include a free tail of that is attached to a housing portion of the control mechanism. FIGS. 10A-B illustrate the housing of the control mechanism 104 with its top cover removed for viewing convenience of the internal linkage components. As the spring linkage 107 rotates, the constant force spring 106a can be unfurled. In one embodiment, the tensioning member 106b or cord is attached to the spring linkage 107 and as the spring linkage 107 rotates, tension is released from the tensioning member 106b. Removing tension from the tensioning member 106b allows the occluding tape member 102 to be drawn out of the housing 105 and remove the circumferential tensioning force from the urethra 152. The flow of urine from the bladder allows expansion of the urethra 152 and further pulls the occluding tape member 102 out of the housing. Thus, pushing the deactivator button 103 to the full extent it can travel causes an "over-center" condition with the center linkage 109 and locks the control mechanism 104 in the deactivated (non-occluded) mode.

In activation, FIG. 10A shows that by pressing the activation button 101 the deactivator button 103 unseats from its locked condition. A spring force generated during the deactivation maneuver rotates the spring linkage 107 in the direction indicated, which rotates the deactivator button 103 in the direction indicated. The force of the constant biasing member 106a on the spring linkage 107 is further transmitted to the tensioning member 106b and the tensioning member 106b is pulled through the conduit tube 106 away from the housing 105. The tensioning member 106b imparts a tension that then pulls the occluding tape member 102 into the housing 105. As a result, the circumference of the occlusive tape member 102 is reduced about the urethra and occludes the urethra with a force equal to the force of the constant force biasing member 106a.

Preferably, the occlusive tape member 102 includes a width dimension that is greater than a thickness dimension to distribute area of the tape member over a larger surface area of the urethra. Preferably, the occlusive tape member is constructed from a 7-15 mil thick polyester woven fabric encapsulated in silicone rubber. This material can prevent elongation under tension, yet maintain the flexibility intended to reduce any tendency for urethral atrophy or erosion. It will be appreciated that these materials are merely exemplary as other materials may be equally or more suitable.

In another embodiment, the occlusive tape member 102 and housing 105 may include a parylene coating thereon. The parylene material can reduce friction between the tape member 102 and the housing 105 into which the tape member 102 is pulled and withdrawn from. The parylene coating may also include a drug coating employing similar principles already described. Parylene and drug eluting coatings, as those described, have been found to reduce capsular formation around implanted silicone devices.

These coatings may be employed to provide the following benefits: (1) Reduction of capsular thickness to maximize the palpability of the activator and deactivator buttons through a patient's skin overlying the implant; (2) Reduction of capsular stiffness so as to ease the deformation of the silicone material overlying the Activation and Deactivation Buttons; (3) Reduction of capsular stiffness so as to reduce the force required to deform any capsule formed and surrounding the occluding tape member as the tape member is retracted within the housing; (4) Reduction of capsular thickness so as to minimize any tendency of the capsule from mechanically blocking tape member passage into (activation) and out of (deactivation) the housing.

As with the control mechanism 14, the control mechanism 104 may be encased in a flexible silicone boot which acts to prevent tissue in-growth. The control mechanism components may be manufactured from an injection molded material such as but not limited to a polyetheretherketone (PEEK) thermoplastic resin. The conduit tube column strength and flexibility may be maintained by employing a coiled or braided MP35N alloy wire. It will be appreciated that these materials are merely exemplary as other materials may be equally or more suitable.

Figure 11A:
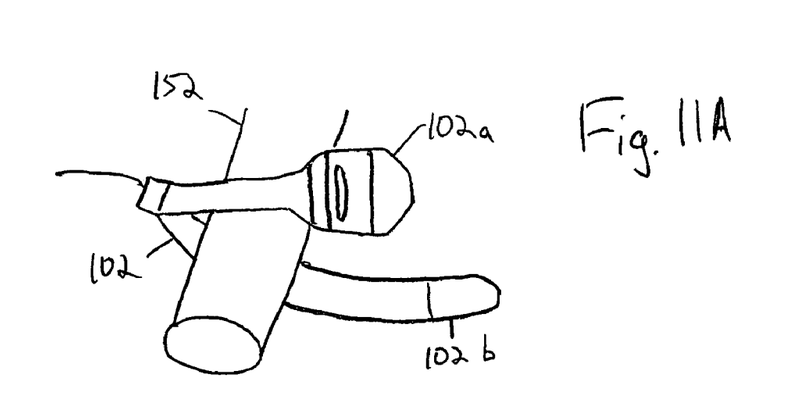
FIG. 11A represents an elevational view of the occluding member of 8A and showing one embodiment of a fastener member included therewith.
Figure 11B:
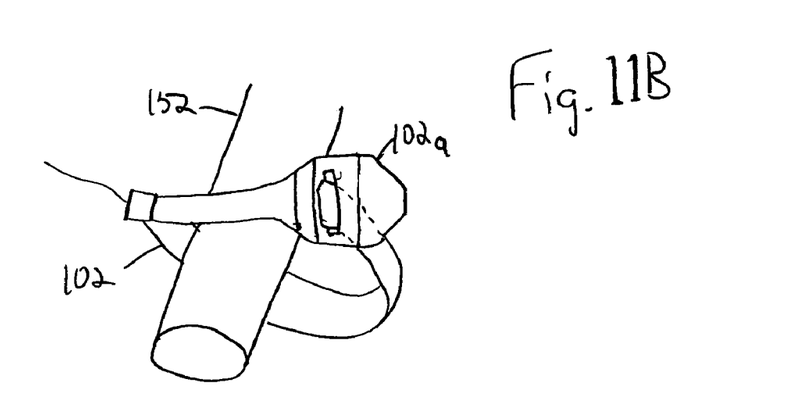
FIG. 11B represents an elevational view of the occluding member and showing the fastener of FIG. 11A being fastened at ends thereof.
Figure 11C:
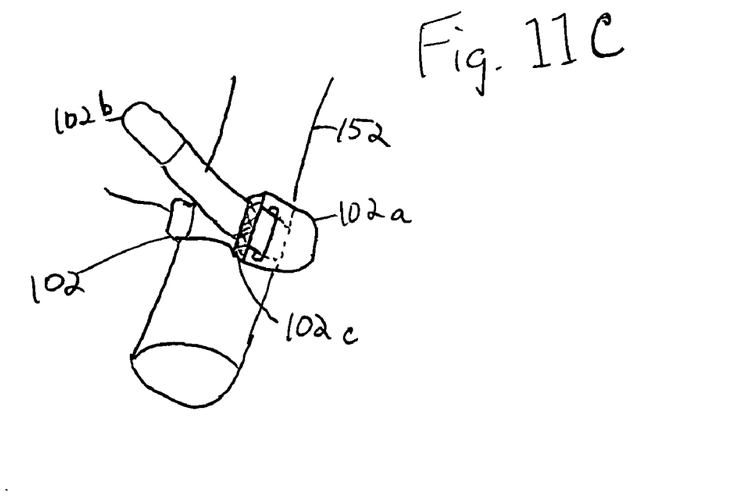
FIG. 11C represents an elevational view of the occluding member and showing the fastener fastened at its ends.

Over-pressurization of the urethra, which could potentially lead to atrophy and erosion, can be prevented by limiting the force applied to the tensioning mechanism. At implantation, a surgeon encircles and custom fits the occluding tape member to the urethra or bladder neck. The surgeon may also employ a belt buckle-like closure mechanism for applying the occluding tape member around the urethra. Such a closure mechanism can provide a simple, intuitive means by which the occluding tape member may be locked in its intended configuration, opened when explanation is required or tightened to prevent recurrent post-operative leakage through a minimally invasive procedure. FIGS. 11A-C illustrate one embodiment of a closure mechanism 102a resembling a buckle-like structure. The closure mechanism 102a may be disposed at one end of the occluding tape member 102 and can fasten with a portion 102b at the other end after being wrapped about the urethra 152 (FIG. 11A). FIG. 11B shows the closure mechanism 102a being fastened with the portion 102b. FIG. 11C shows the closure mechanism 102a in the fastened state with the portion 102b. Sutures 102c may be employed to lock the closure mechanism in place. It will be appreciated that the configuration shown in FIGS. 11A-C is merely, as other mechanical fastening structures may be employed that are equally or more suitable.

The present disclosure herein described provides an improved incontinence device wherein the drug coating can minimize capsular formation resulting from a bodily response of the host. In turn, the drug coating can facilitate function of the incontinence device in preventing urinary or bowel leakage by preventing the structures of the device from being impeded by any capsular formation.

The above specification provides a complete description of the composition, manufacture and use of the improved penile compression device in accordance with the principles of the present invention. Since many embodiments of the inventive principles can be made without departing from their spirit and scope, the invention of the present disclosure resides in the claims hereinafter appended.

The invention claimed is:

1. An incontinence device for preventing urinary, bowel or esophageal leakage comprising:
   an occluding member adapted to be implanted in a host and adapted to be disposed around a bodily duct for exiting waste;
   a control mechanism operatively connected with the occluding member, the control mechanism including an activator and a deactivator, the control mechanism adapted to be implanted in the host and to control the occluding member so as to close the bodily duct in an occluded state or open the bodily duct in a non-occluded state; and a drug coating including a bioaffecting composition thereon, the drug coating being disposed as a layer on an outer surface of both the occluding member and the control mechanism including the activator and deactivator, the drug coating capable of eluting the bioaffecting composition into surrounding tissue of the host, wherein the drug coating minimizes capsular formation resulting from a bodily response of the host and the drug coating facilitates function of the incontinence device in preventing urinary or bowel leakage, wherein the occluding member includes a tape member having first and second ends adapted to encircle the bodily duct after being implanted, the tape member having a preset radial occlusive force imparted thereon to suitably contract and close the bodily duct, wherein the tape member is connected to a housing, the housing having an inner space for receiving the first and second ends of the tape member when the tape member exerts its preset radial occlusive force to close the bodily duct, and for releasing the first and second ends of the tape member from its preset radial occlusive force to open the bodily duct, and wherein the control mechanism includes a tensioning member controlled by the activator and deactivator, the tensioning member being connected to the first and second ends of the tape member to move the tape member to the occluded state when the activator is used and to move the tape member to the non-occluded state when the deactivator is used.

2. The incontinence device of claim 1, wherein the tape member including a width dimension that is greater than a thickness dimension.

3. The incontinence device of claim 1, wherein the deactivator releases the tape member from the occluded state by releasing a tension from the tensioning member and the activator returns the tape member to the occluded state by returning tension to the tensioning member.

4. The incontinence device of claim 1, wherein the activator and deactivator are buttons connected to the tensioning member by a mechanical linkage assembly.

5. The incontinence device of claim 1, wherein the deactivator is a plunger mechanism.

6. The incontinence device of claim 1, wherein the drug coating being configured as a polymeric layer that is adherent to the outer surface of at the occluding member and the control mechanism, the layer holding the bioaffecting composition within its polymeric interstices.

7. The incontinence device of claim 1, wherein the drug coating including a porous polymeric membrane disposed over the drug coating, the porous membrane including a pore size that controls an elution rate of the bioaffecting composition.

8. The incontinence device of claim 1, wherein the drug coating comprises a silicone matrix and the bioaffecting composition consisting of at least one of rapamycin and dexamethasone.

9. A urinary incontinence device comprising:

a tape member adapted to be implanted in a host and adapted to be disposed around a urethra, the tape member having first and second ends adapted to encircle the urethra after being implanted, the tape member having a preset radial occlusive force imparted thereon to suitably contract and close the urethra;

a control mechanism operatively connected with the tape member, the control mechanism including an activator button and a deactivator button, the control mechanism adapted to be implanted in the host and to control the tape member to close the urethra in an occluded state or open the urethra in a non-occluded state; and a drug coating including a bioaffecting composition thereon, the drug coating being disposed as a layer on an outer surface of both the tape member and the control mechanism including the activator button and deactivator button, the drug coating capable of eluting the bioaffecting composition into surrounding tissue of the host, wherein the drug coating minimizes capsular formation resulting from a bodily response of the host and the drug coating facilitates function of the incontinence device in preventing urinary leakage wherein the tape member is connected to a housing, the housing having an inner space for receiving the first and second ends of the tape member when the tape member exerts its preset radial occlusive force to close the urethra, and for releasing the first and second ends of the tape member from its preset radial occlusive force to open the urethra, and wherein the control mechanism includes a tensioning member controlled by the activator and deactivator buttons, the deactivator button moves the tape member from the occluded state to the non-occluded state by releasing tension from the tensioning member thereby releasing the reset radial occlusive force of the tape member on the urethra, and the activator button returns the tape member to the occluded state from the non-occluded state by returning tension to the tensioning member thereby returning the preset radial occlusive force of the tape member on the urethra.

10. The incontinence device of claim 9, wherein the tape member including a width dimension that is greater than a thickness dimension.

11. The incontinence device of claim 9, wherein the tape member comprises a polyester woven fabric encapsulated in a silicone rubber.

12. The incontinence device of claim 9, wherein the drug coating including a porous polymeric membrane disposed over the drug coating, the porous membrane including a pore size that controls an elution rate of the bioaffecting composition.

13. A method of controlling a bodily duct to enable or disable urine, bowel or esophageal movement comprising:

implanting an incontinence device into a bodily host, the incontinence device including an occluding member adapted to be implanted in a host and adapted to be disposed around a bodily duct; a control mechanism operatively connected with the occluding member, the control mechanism including an activator and a deactivator, the control mechanism adapted to be implanted in the host and to control the occluding member so as to close the bodily duct in a occluded state or open the bodily duct in a non-occluded state; and a drug coating including a bioaffecting composition thereon, the drug coating being disposed as a layer on a outer surface of both the occluding member and the control mechanism including the activator and deactivator, the drug coating capable of eluting the bioaffecting composition into surrounding tissue of the host, wherein the drug coating minimizes capsular formation resulting from a bodily response of the host and the drug coating facilitates function of the incontinence device in preventing urinary, bowel, or esophageal leakage, wherein the occluding member includes a tape member having first and second ends adapted to encircle the bodily duct after being implanted, the tape member having a preset radial occlusive force imparted thereon to suitably contract and close the bodily duct, wherein the tape member is connected to a housing, the housing having an inner space for receiving the first and second ends of the tape member when the tape member exerts its preset radial occlusive force to close the bodily duct, and for releasing the first and second ends of the tape member from its preset radial occlusive force to open the bodily duct, and wherein the control mechanism includes a tensioning member controlled by the activator and deactivator, the tensioning member being connected to the first and second ends of the tape member to move the tape member to the occluded state when the activator is used and to move the tape member to the non-occluded state when the deactivator is used;

activating the incontinence device, using the activator of the control mechanism, to move the occluding member to an occluded state, thereby disabling urine, bowel or esophagus leakage;

deactivating the incontinence device, using the deactivator of the control mechanism, to move the occluding member to a non-occluded state, thereby enabling urine, bowel or esophagus leakage; and eluting the bioaffecting composition into surrounding tissue of the bodily host, wherein the bioaffecting composition minimizing capsular formation about the incontinence device, so as to prevent impeding the function of the incontinence device.

* * * * *